(12) United States Patent
Tanaka et al.

(10) Patent No.: US 11,474,088 B2
(45) Date of Patent: Oct. 18, 2022

(54) METHOD FOR DETERMINING ORIGIN OF AMINO ACID

(71) Applicant: NISSIN FOODS HOLDINGS CO., LTD., Osaka (JP)

(72) Inventors: Masaharu Tanaka, Osaka (JP); Yoichi Yatsukawa, Osaka (JP); Kazuhiro Kobayashi, Osaka (JP); Soichi Tanabe, Osaka (JP); Mitsuru Tanaka, Osaka (JP)

(73) Assignee: NISSIN FOODS HOLDINGS CO., LTD., Osaka (JP)

( * ) Notice: Subject to any disclaimer, the term of this patent is extended or adjusted under 35 U.S.C. 154(b) by 414 days.

(21) Appl. No.: 16/483,192

(22) PCT Filed: Jan. 31, 2018

(86) PCT No.: PCT/JP2018/003082
§ 371 (c)(1),
(2) Date: Aug. 2, 2019

(87) PCT Pub. No.: WO2018/143226
PCT Pub. Date: Aug. 9, 2018

(65) Prior Publication Data
US 2019/0360983 A1    Nov. 28, 2019

(30) Foreign Application Priority Data
Feb. 6, 2017 (JP) .............. JP2017-019817

(51) Int. Cl.
*G01N 27/62* (2021.01)
*G01N 30/72* (2006.01)
(Continued)

(52) U.S. Cl.
CPC .............. *G01N 30/88* (2013.01); *G01N 27/62* (2013.01); *G01N 30/72* (2013.01);
(Continued)

(58) Field of Classification Search
CPC .... G01N 27/62; G01N 30/72; G01N 33/6848; G01N 33/6812; G01N 30/88; G01N 30/7206; G01N 31/12
(Continued)

(56) References Cited

U.S. PATENT DOCUMENTS

| 4,916,313 A * | 4/1990 | Hall ................ G01N 30/7206 250/282 |
| 5,424,539 A * | 6/1995 | Brand ................ G01N 30/10 250/282 |
| 5,432,344 A * | 7/1995 | Brand ............ G01N 30/7206 250/288 |

FOREIGN PATENT DOCUMENTS

| JP | 2010-216892 | 9/2010 |
| JP | 2012-251899 | 12/2012 |

OTHER PUBLICATIONS

Kyrklund, T., Lipids 1987, 22, 274-277.*
(Continued)

*Primary Examiner* — Arlen Soderquist
(74) *Attorney, Agent, or Firm* — Hamre, Schumann, Mueller & Larson, P.C.

(57) ABSTRACT

The present invention relates to a method for determining the origin of glutamic acid in a sample and, in a broader sense, relates to a method for determining the origin of an amino acid. The present invention makes it possible to measure the stable isotope ratio, with a considerably higher accuracy than that of conventional methods, by measuring the δ13C of glutamic acid (amino acid) by elemental analysis-stable isotope ratio mass spectrometry (EA-IRMS) and measuring the δ15N by gas chromatography-stable isotope ratio mass spectrometry (GC-IRMS). In addition, the present invention makes it possible to determine the origin of glutamic acid (amino acid) by comparing the stable isotope ratio of the glutamic acid (amino acid) whose origin is (Continued)

unclear with the stable isotope ratio of glutamic acid (amino acid) whose origin is clear.

10 Claims, 1 Drawing Sheet

(51) Int. Cl.
| | |
|---|---|
| *G01N 33/68* | (2006.01) |
| *G01N 30/88* | (2006.01) |
| *G01N 31/12* | (2006.01) |
| *G01N 30/02* | (2006.01) |

(52) U.S. Cl.
CPC ... *G01N 33/6848* (2013.01); *G01N 2030/025* (2013.01); *G01N 2030/8818* (2013.01); *G01N 2030/8868* (2013.01)

(58) Field of Classification Search
USPC .......................................................... 436/161
See application file for complete search history.

(56) References Cited

OTHER PUBLICATIONS

Fry, B. et al, Analytical Chemistry 1992, 64, 288-291.*
Fantie, M. S. et al, Oecologia 1999, 120, 416-426.*
Manca, G. et al, Journal of Agriculture and Food Chemistry 2001, 49, 1404-1409.*
Peteranderl, R. et al, Journal of the American Society for Mass Spectrometry 2004, 15, 478-485.*
Estrada, J. A. et al, Marine Biology 2005, 147, 37-45.*
Petzke, K. J. et al, Journal of Nutrition 2005, 135, 1515-1520.*
Bodin, N. et al, Journal of Experimental Marine Biology and Ecology 2007, 341, 168-175.*
Lorrain, A. et al, Marine Ecology Progress Series 2001, 391, 293-306.*
Ogawa, N. O. et al., "Ultra-sensitive elemental analyzer/isotope ratio mass spectrometer for stable nitrogen and carbon isotope analyses" in Earth, Life and Isotopes. Ohkouchi, N. et al, eds., Kyoto University Press, 2010, 339-353.*
Tayasu, I. et al, Limnology 2011, 12, 261-266.*
Ryan, C. et al, Rapid Communications in Mass Spectrometry 2012, 26, 2745-2754.*
Miyagi, A. et al, Journal of Food Engineering 2013, 116, 749-757.*
Todoroki, K. et al, Journal of Agriculture and Food Chemistry 2014, 62, 6206-6211.*
McGregor, R. F. et al, Clinica Chimica Acta 1973, 48, 65-75.*
Barakat, M. F. et al, Microchemical Journal 1980, 25, 471-484.*
Hare, P. E. et al, Journal of Archaeological Science 1991, 18, 277-292.*
Tripp, J. A. et al, Journal of Separation Science 2006, 29, 41-48.*
Ogawa, N. O. et al, in "Earth, Life, and Isotopes" Ohkouchi, N. et al eds., Kyoto University Press 2010, 339-353.*
Kamath, T. et al., American Geophysical Union, Fall Meeting 2012, abstract id. ED31A-0700, one page.*
Broek, T. A. B. et al, Rapid Communications in Mass Spectrometry 2013, 27, 2327-2337.*
Broek, T. A. B. et al, Limnology and Oceanography: Methods 2014, 12, 840-852.*
Tan, M. et al, Journal of Chinese Mass Spectrometry Society 2015, 36, 334-340.*
Robert G. Walsh et al., "Compound-specific [delta]13C and [delta]15N analysis of amino acids: a rapid, chloroformate-based method for ecological studies", Rapid Communications in Mass Spectrometry, vol. 28, No. 1, Jan. 15, 2014, pp. 96-108.
Mauro Paolini et al., "Compound-Specific [delta]15N and [delta]13C Analyses of Amino Acids for Potential Discrimination between Organically and Conventionally Grown Wheat", Journal of Agricultural and Food Chemistry, vol. 63, No. 25, May 25, 2015, pp. 5841-5850.
Gemma Molero et al., "Measurement of 13C and 15N isotope labeling by gas chromatography/combustion/isotope ratio mass spectrometry to study amino acid fluxes in a plant-microbe symbiotic association", Rapid Communications in Mass Spectrometry, vol. 25, No. 5, Mar. 15, 2011, pp. 599-607.
E. Federherr et al., "A novel high-temperature combustion interface for compound-specific stable isotope analysis of carbon and nitrogen via high-performance liquid chromatography/isotope ratio mass spectrometry", Rapid Communications in Mass Spectrometry, vol. 30, No. 7, Feb. 29, 2016, pp. 944-952.
James F. Carter et al., "Isotopic characterisation of 3,4-methylenedioxyamphetamine and 3,4-methylenedioxymethylamphetamine (ecstasy)", The Analyst, vol. 127, No. 6, May 14, 2002, pp. 830-833.
The extended European search report issued for the European Patent Application No. 18748328.4, dated Jan. 14, 2021, 10 pages.
Chikaraishi, et al., Compound-specific isotope analysis (CSIA) by gas chromatograph/isotope ratio mass spectrometer (GC/IRMS), Res. Org. Geochem., 23-24, 99-122, 2008.
Takano, et al., "Quality control by wet chemical pre-treatment for precise compound-specific isotope analysis", Res. Org. Geochem., 26, 81-93, 2010.
International Search Report issued in International Application No. PCT/JP2018/003082, dated Mar. 13, 2018, 6 pages.
Written Opinion issued in International Application No. PCT/JP2018/003082, dated Mar. 13, 2018, 3 pages.
Chikaraishi, et al., "Amino acid (pivaloyl/isopropyl ester derivative) analysis by GC/MS" Res. Org. Geochem., 25, 61-70, 2009 English translation provided.

* cited by examiner

METHOD FOR DETERMINING ORIGIN OF AMINO ACID

TECHNICAL FIELD

The present invention relates to a method for determining the origin of glutamic acid in a sample and, in a broader sense, relates to a method for determining the origin of an amino acid.

BACKGROUND ART

An amino acid is a one of organic compound having both an amino group and a carboxyl group in one molecule and is contained in many foods. Above all, salts of glutamic acid and aspartic acid are known as typical umami components, and, in particular, glutamates have become to be used in processed food products all over the world with the spread of Japanese food.

Glutamates are industrially produced usually by a fermentation process in which molasses, starch, and so on of sugar cane are fermented to produce glutamic acid, and the glutamic acid is crystallized as monosodium glutamate (MSG) to be easily dissolved in water. MSG and glutamates obtained by hydrolyzing protein contained in, for example, kelp differ from each other in the point that the former (MSG) contains almost no minerals other than sodium, whereas the latter contains minerals (e.g., calcium and potassium) in addition to sodium.

By the way, in recent years, the traceability of food is regarded as important, and there is also a demand for amino acids derived from meat to be removed by religious reasons. In addition, as described above, since MSG contains almost no minerals other than sodium, sodium is prone to be overdosed. Accordingly, there is a demand for suppressing the amount of use of industrial products, such as MSG.

As a method for determining the origin (such as raw material and original production area) of food, a method for determining the origin of glucosamine by elemental analysis-isotope ratio mass spectrometry (EA-IRMS) has been disclosed (Patent Literature 1). However, this method is not supposed to analyze organic compounds having both an amino group and a carboxyl group in one molecule, such as amino acids. Consequently, there is no disclosure about the process of purifying a sample, and it is difficult to accurately measure the stable isotope ratio of an amino acid.

In addition, as a method for measuring the stable isotope ratio of an amino acid, a method in which an amino acid is derivatized to pivaloyl/isopropyl ester for measuring the stable isotope ratio of the amino acid by gas chromatography-isotope ratio mass spectrometry (GC-IRMS) has been disclosed (Non Patent Literature 1 and Patent Literature 2). This method can measure the isotope ratios of multiple amino acids at a time, and the accuracy thereof is high. Therefore, it is a very excellent method.

However, in this method, carbon not derived from amino acid but derived from pivaloyl chloride and isopropanol are introduced in the process of derivatization. Accordingly, the stable carbon isotope ratio cannot be accurately measured.

CITATION LIST

Patent Literature

Patent Literature 1: Japanese Patent Laid-Open No. 2012-251899
Patent Literature 2: Japanese Patent Laid-Open No. 2010-216892

Non Patent Literature

Non Patent Literature 1: Res. Org. Geochem., 25, 61-79, (2009), "GC/MS analysis of amino acids as pivaloyl/isopropylesters"
Non Patent Literature 2: Res. Org. GeoChem., 23/24, 99-122, (2008), "Compound-specific isotope analysis (CSIA) by gas chromatograph/isotope ratio mass spectrometer (GC/IRMS)"
Non Patent Literature 3: Res. Org. GeoChem., 26, 81-93, (2010), "Quality control by wet chemical pre-treatment for precise compound-specific isotope analysis"

SUMMARY OF INVENTION

Technical Problem

The present invention provides, in view of importance of traceability, a method for determining the origin of an amino acid and a method for measuring the same.

Solution to Problem

The present inventors have made it possible to measure the stable isotope ratio of an amino acid, with a considerably higher accuracy than that of conventional methods, by measuring the stable carbon isotope ratio (hereinafter referred to as "$\delta 13C$") of the amino acid by elemental analysis-stable isotope ratio mass spectrometry (hereinafter referred to as "EA-IRMS") and measuring the stable nitrogen isotope ratio (hereinafter referred to as "$\delta 15N$") of the amino acid by gas chromatography-stable isotope ratio mass spectrometry (hereinafter referred to as "GC-IRMS"), and also made it possible to determine the origin of an amino acid.

Advantageous Effects of Invention

According to the present invention, it is possible to accurately measure the stable isotope ratio of an amino acid and to determine the origin of an amino acid.

DESCRIPTION OF EMBODIMENTS

Figure 1:
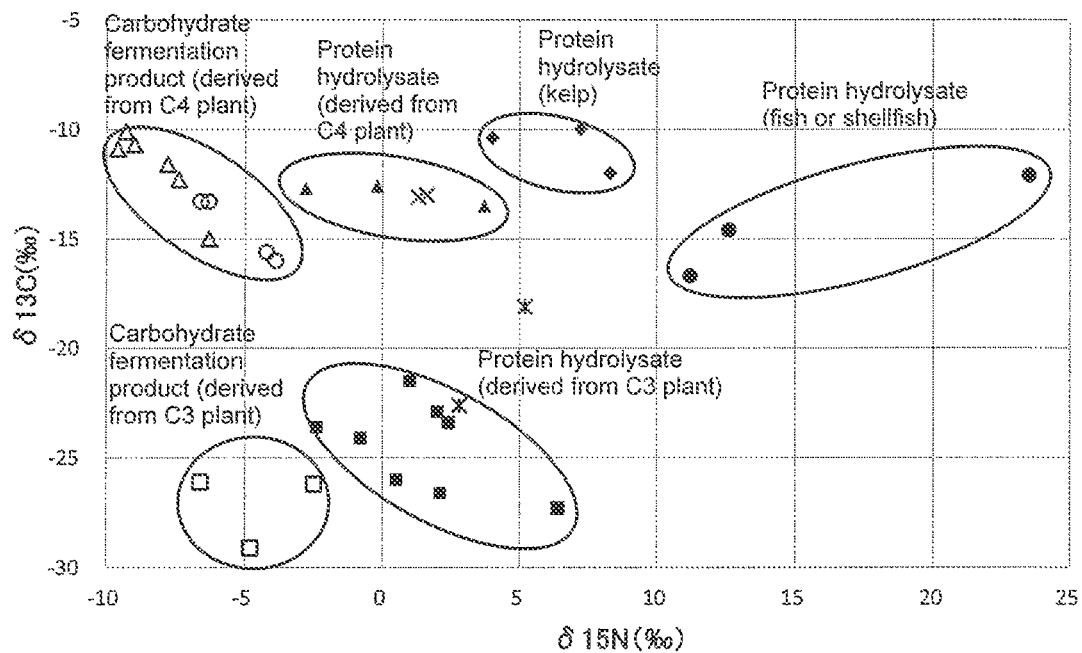
FIG. 1 is a graph plotting the stable isotope ratios of glutamic acid contained in samples whose origins are clear.

The present invention makes it possible to measure the stable isotope ratio of an amino acid with a considerably higher accuracy than that of conventional methods by measuring the $\delta 13C$ of the amino acid by EA-IRMS and measuring the $\delta 15N$ by GC-IRMS. In addition, the origin of an amino acid is determined by comparing the stable isotope ratio of the amino acid whose origin is unclear with the stable isotope ratios of amino acids whose origins are clear.

In the present specification, the term "amino acid" refers to a one of organic compound having both an amino group and a carboxyl group as functional groups, and examples thereof include aspartic acid, glutamic acid, and glycine. In addition, the term "amino acid" in the present invention includes amino acid salts unless otherwise stated. Specifically, for example, monosodium glutamate, calcium glutamate, and potassium glutamate are treated as amino acids.

The present invention is characterized in that δ13C is measured by elemental analysis-stable isotope ratio mass spectrometry (EA-IRMS) and δ15N is measure by gas chromatography-stable isotope ratio mass spectrometry (GC-IRMS). Methods for measuring δ13C and δ15N will now be specifically described.

(Sample)

The sample of the present invention is amino acid-containing food (including umami seasoning, reagent, and so on). When protein contained in a sample is not decomposed into amino acids, the protein is required to be hydrolyzed in advance as pretreatment. The protein may be hydrolyzed by any method, and a known method can be used. For example, a method in which an appropriate amount of hydrogen chloride is added to a sample and the sample is heated to decompose the protein into amino acids can be used.

(Method for Calculating Stable Isotope Ratio)

The stable isotope ratio in a sample is defined by per mil deviation (δ value, unit: ‰ (per mil)) against the stable isotope ratio of an international standard substance shown in the following expression 1:

$$\delta \text{ value} = [(R \text{ sample}/R \text{ international standard substance})-1] \times 1000 (‰)$$ Expression 1:

As the standard substances, Cretaceous Pee Dee layer belemnite carbonate is used for carbon, and nitrogen gas in the atmosphere is used for nitrogen, and the δ values are written as δ13C and δ15N, respectively.

(Measurement of Stable Nitrogen Isotope Ratio (δ15N))

As described above, the δ15N of an amino acid can be measured by gas chromatography-stable isotope ratio mass spectrometry (GC-IRMS) (see Non Patent Literatures 1 and 2). GC-IRMS can measure stable isotope ratios of multiple amino acids at a time, and the accuracy thereof is very high. Therefore, it is a very useful method.

The δ15N is preferably measured through an extraction step (A1), a degreasing step (A2), a cation exchange step (A3), a derivatization step (A4), and a GC-IRMS step (A5). However, the extraction step (A1) and the degreasing step (A2) are not essential steps. For example, the degreasing step (A2) is unnecessary for a sample containing almost no lipids.

First, the extraction step (A1) will be described. In the extraction step, a hydrogen chloride solution or the like is added to a sample, the mixture is stirred and centrifuged, and the precipitated insoluble components are removed. If the sample contains a large amount of insoluble components, a trouble, such as column clogging, may be caused in the subsequent steps. Accordingly, it is preferable to remove most insoluble components in advance by centrifugation.

Next, in the degreasing step (A2), the sample is degreased by liquid-liquid extraction using water and an organic solvent (for example, "dichloromethane/n-hexane").

Next, the cation exchange step (A3) will be described. In the cation exchange step, the amino acid in the sample is adsorbed to a cation-exchange column, the components (impurities) not adsorbed to the column are washed out, and the amino acid is desorbed from the column and is collected. The cation-exchange column (column-like shape) can be replaced by a cation-exchange resin (amorphous shape) or a cation-exchange membrane (membrane-like shape).

The cation exchange step (A3) will be described in more detail. First, for example, hydrogen chloride is added to a sample for cationization of an amino acid. Subsequently, the sample (containing the cationized amino acids) is passed through a cation-exchange column. Consequently, the cationized amino acid is adsorbed to the column, and uncationized components (such as carbohydrates) are not adsorbed to the column. Accordingly, the components not adsorbed to the column can be removed by passing, for example, distilled water through the column.

Next, weakly basic aqueous ammonia is added to the column to desorb and collect the amino acid from the column. On this occasion, since the amino acid is dissolved in the aqueous ammonia, the solution is evaporated to dryness by a known method, such as nitrogen-blowing high-speed concentration in order to remove the aqueous ammonia.

Next, the derivatization step (A4) will be described. In order to perform accurate measurement by gas chromatography (GC), generally, a sample is required to be gasified at about 300° C. or less and converted to a derivative that is not thermally decomposed. In this regard, amino acids are organic compounds having both an amino group and a carboxyl group in one molecule and therefore have strong ionic bonds and low volatility. Accordingly, in order to obtain accurate data by GC-IRMS, amino acids are required to be derivatized to increase the volatility.

Examples of a known method for derivatization include a tert-butyl dimethyl silyl derivative method, a trifluoroacyl/isopropyl ester derivative method, a pentafluoroacyl/isopropyl ester derivative method, a pivaloyl/isopropyl ester derivative method, and an ethoxycarbonyl/ethyl ester derivative method.

In the present invention, among these derivatization methods, preferred is the pivaloyl/isopropyl ester derivative method. In the pivaloyl/isopropyl ester derivative method, since the derivative group does not contain silicon, fluorine, and the like and has a relatively large number of carbon atoms, the derivatized amino acid is relatively stable and is hardly thermally decomposed, and the method is therefore suitable for measurement by gas chromatography.

Finally, the GC-IRMS step (A5) will be described. Typical specification and measurement procedure of GC-IRMS will be described here, but they are not limited thereto. First, the amino acid derivative described above is adjusted to an appropriate concentration with, for example, dichloromethane and is poured into a column together with a carrier gas (e.g., helium gas). The amino acid derivative is carried inside the column together with the carrier gas, and the moving speed is different among compounds. Therefore the arrival times of the components (for example, a glutamic acid derivative and an aspartic acid derivative) at the outlet of the column are different from each other to allow separation of the components from one another. The separated amino acid derivatives are continuously introduced into a reactor (combustion furnace/reduction furnace) directly connected to the column.

The introduced amino acid derivatives are each oxidatively decomposed to $N_2$, $N_xO_y$ (nitrogen oxide), $H_2O$, and $CO_2$ in the combustion furnace (temperature: 800° C. to 1150° C.), and the $N_xO_y$ is further reduced to nitrogen gas ($N_2$) in the reduction furnace (temperature: 550° C. to 650° C.). Furthermore, $H_2O$ is removed by a water-permeable filter, $CO_2$ is removed by liquid-nitrogen trap, $N_2$ is then introduced into an IRMS system together with a carrier gas, and the isotope ratio of $N_2$ is measured. Since $CO_2$ generates $CO^+$ (m/z28) by ionization, it is necessary to remove $CO_2$ before the measurement.

A reactor that simultaneously performs oxidation and reduction of amino acid derivatives may be used. In such a case, the temperature of the reactor (reactor temperature) is about 800° C. to 1150° C.

From the viewpoint of accurately measuring an isotope ratio, the temperature of the combustion furnace is preferably 950° C. to 1050° C. Insufficient oxidation causes generation of CO gas of the same mass as $N_2$ gas, which becomes an obstacle to accurate measurement of the isotope ratio. In contrast, since peroxidation increases the rate of generation of nitrogen oxides other than $N_2$, there is a risk that not all peroxides are reduced in the reduction furnace, which becomes an obstacle to accurate measurement of the isotope ratio.

(Measurement of Stable Carbon Isotope Ratio ($\delta 13C$))

As described above, the $\delta 15N$ of an amino acid can be measured by GC-IRMS. However, the measurement of the stable isotope ratio of an amino acid by GC-IRMS requires derivatization of the amino acid and introduction of carbon derived from a derivatizing reagent (such as pivaloyl group). Accordingly, the result of $\delta 13C$ measurement is affected by carbon derived from the derivatizing reagent, and the accuracy thereof is reduced. A reduction in the accuracy becomes significant with an increase in the molecular weight of the derivatizing reagent, in other words, the accuracy is reduced by increasing the thermal stability of the amino acid derivative. Accordingly, GC-IRMS cannot accurately measure the $\delta 13C$.

Due to the above-described reasons, in the present invention, it is necessary to measure the $\delta 13C$ of an amino acid by elemental analysis-stable isotope ratio mass spectrometry (EA-IRMS). The measurement by EA-IRMS will now be described in detail.

In the measurement by GC-IRMS, even if the sample contains impurities that do not volatilize at about 300° C., the isotope analysis is not affected, and a specific amino acid (e.g., glutamic acid) can be isolated by gas chromatography (GC). Accordingly, the burden by purification of the sample is low.

In contrast, the measurement by EA-IRMS is largely affected by impurities that burn at about 1000° C. and amino acids other than the amino acid (e.g. glutamic acid) as the measurement target. Accordingly, the measurement of the $\delta 13C$ of a specific amino acid by EA-IRMS is preferably performed through an extraction step (B1), a degreasing step (B2), a column purification step (B3), a cation exchange step (B4), a separation step (B5), and an EA-IRMS step (B6).

First, the extraction step (B1) will be described. In the extraction step, a hydrogen chloride solution or the like is added to a sample, the mixture is stirred and centrifuged, and the precipitated insoluble components are removed. If the sample contains a large amount of insoluble components, a trouble, such as column clogging, may be caused in the subsequent steps. Accordingly, it is preferable to remove most insoluble components in advance by centrifugation.

Next, the degreasing step (B2) will be described. In the degreasing step, the sample is degreased by liquid-liquid extraction using water and an organic solvent (for example, "dichloromethane/n-hexane").

Next, the column purification step (B3) will be described. The column purification step (B3) is composed of a reverse phase chromatography purification step (B3-1) and a decolorization step (B3-2).

In the reverse phase chromatography purification step (B3-1), low-polar substances, such as lipids, are separated by reverse phase chromatography. Since the polarity of lipids is lower than that of glutamic acid, lipids can be efficiently separated by reverse phase chromatography (the elution speed increases with an increase in the polarity). The conditions for the reverse phase chromatography are, for example, an ODS column as the stationary phase and water or alcohol as the mobile phase.

Next, in the decolorization step (B3-2), the dissolved sample is passed through activated carbon to remove a compound having a cyclic structure, such as a pigment, contained in the sample. Since compounds having a cyclic structure are often colored, the term "decolorization" is used. However, a compound having a cyclic structure is removed by this step, even if the compound is colorless. Although the activated carbon may have any shape (such as, amorphous, column-like, or membrane-like shape), a column-like shape is preferred in consideration of workability and so on.

Next, the cation exchange step (B4) will be described. The cation exchange step (B4) is a purification step in which the amino acid in the sample is adsorbed to a cation-exchange column, the impurities not adsorbed to the column is washed out, and the amino acid is desorbed and collected from the column finally. Specifically, the purification method is as described in the "cation exchange step (A3)".

Next, the separation step (B5) will be described. In the separation step (B5), only a specific amino acid is separated and purified from the extracted and degreased sample by hydrophilic interaction liquid chromatography (HILIC). Since the polarity of amino acids is too high, separation and purification by reverse phase chromatography are difficult. Accordingly, it is preferable to separate and purify a specific amino acid by HILIC. The conditions for the HILIC are, for example, a gel prepared by binding an amino group to a polymer as the stationary phase and an aqueous ammonium hydrogen carbonate solution/methanol mixture solution as the mobile phase.

Finally, the EA-IRMS step (B6) will be described. Here, typical specification and measurement procedure of EA-IRMS will be described, but they are not limited thereto.

It is repetition, but since the EA-IRMS system does not include a mechanism for separating amino acids, it is necessary to use a specific amino acid separated and purified from a sample in advance for the measurement. In the following description about the EA-IRMS step (B6), the amino acid and the amino acid salt to be used for EA-IRMS are collectively referred to as "amino acid sample".

The amino acid sample introduced into an elemental analyzer (EA) is oxidatively decomposed to $N_2$, $N_xO_y$ (nitrogen oxide), $H_2O$, and $CO_2$ in the combustion furnace, and $N_xO_y$ is further reduced to nitrogen gas ($N_2$) in the reduction furnace (temperature: 550° C. to 700° C.). $H_2O$ is removed by water trap ($Mg(ClO_4)_2$), and $CO_2$ and $N_2$ are then introduced into an IRMS system together with a carrier gas, and the stable isotope ratio of $CO_2$ is measured.

Here, the reasons that $\delta 13C$ cannot be accurately measured by GC-IRMS and the reasons that $\delta 15N$ cannot be accurately measured by EA-IRMS will be collectively described.

(Reasons that $\delta 13C$ Cannot be Accurately Measured by GC-IRMS)

As described above, in order to measure the stable isotope ratio of an amino acid by GC-IRMS, derivatization of the amino acid is required, and a carbon atom derived from a derivatizing reagent (such as pivaloyl group) is introduced into the amino acid. Accordingly, when the δ13C of an amino acid is measured by GC-IRMS, correction calculation is required, resulting in a reduction in the accuracy. In addition, isotope fractionation of δ13C may occur during the derivatization or separation with a GC column.

(Reasons that δ15N Cannot be Accurately Measured by EA-IRMS)

Ammonia derived from ammonium hydrogen carbonate used as the mobile phase is added to the carboxyl group of amino acid crystals obtained in a pretreatment step to form a salt, resulting in introduction of a nitrogen atom. Accordingly, correction calculation is required, resulting in a reduction in the accuracy. In addition, isotope fractionation of δ15N may occur during the purification by reverse phase chromatography in the pretreatment step or the separation step by HILIC.

The isotope fractionation is a change in the stable isotope ratio through chemical or physical process. In order to accurately analyze the stable isotope ratio of a sample, the pretreatment method needs to be selected to cause isotope fractionation as low as possible.

(Origin-Determining Procedure)

A procedure for determining the origin of an amino acid will be described using glutamic acid as an example. The origin of glutamic acid can be determined by (1) measuring the stable isotope ratios (δ13C and δ15N) of glutamic acid whose origin is clear, then (2) measuring the stable isotope ratios of glutamic acid whose origin is unclear contained in a sample, and finally (3) comparing the stable isotope ratios of both samples. Since the isotope ratios differ depending on the production area and the raw material, it is preferable to accumulate data of glutamic acid whose origin is clear as much as possible.

EXAMPLES

A method for measuring the stable isotope ratio of an amino acid and a method for determining the origin of the amino acid will now be described using glutamic acid as an example, but the present invention is not limited to the following examples.

<Purification Method>

(1) Hydrolysis of Sample

Distilled water and 12 M hydrogen chloride were added to a sample, followed by treatment at 110° C. for 12 to 24 hours to decompose the protein contained in the sample into amino acids. Subsequently, the sample was centrifuged, and the supernatant was collected. The amounts of the sample, distilled water, and hydrogen chloride were appropriately changed according to the amount of glutamic acid that can be separated and purified from a sample.

(2) Measurement of Stable Nitrogen Isotope Ratio (δ15N)

The process for measuring the stable nitrogen isotope ratio (δ15N) of glutamic acid is as follows.

Extraction Step (A1)

Distilled water and 1 M hydrogen chloride were added to a sample, followed by stirring for 10 minutes and then centrifugation. The precipitated insoluble components were removed.

Degreasing Step (A2)

To the aqueous solution from which the insoluble components were removed was added a dichloromethane/n-hexane mixed solvent to perform liquid-liquid extraction. On this occasion, since an amino acid and fat or oil are selectively dissolved in the aqueous layer and the organic layer, respectively, the fat or oil was removed by collecting the aqueous layer only.

Cation Exchange Step (A3)

The amino acid was extracted under the following conditions:

Sample-cationizing agent: hydrogen chloride,
Stationary phase: "AG50W-X8 200-400 mesh Resin" manufactured by Bio-Rad Laboratories, Inc., and
Mobile phase: distilled water for removing impurities, and 10% ammonia solution for collecting the amino acid.

Derivatization Step (A4)

2-Propanol/thionyl chloride (4:1) was added to the sample, followed by heating at 110° C. for 2 hours to esterify the carbonyl group of the amino acid. Subsequently, pivaloyl chloride/dichloromethane (1:4) was added thereto, followed by heating at 110° C. for 2 hours to pivaloylate the amino group to obtain an amino acid derivative.

GC-IRMS Step (A5)

The amino acid derivative was introduced into a GC-IRMS system, and the δ15N was measured. The specification and the measurement conditions of the GC-IRMS system (manufactured by Thermo Fisher Scientific) were as shown in Table 1.

TABLE 1

| | |
|---|---|
| Gas chromatograph | TRACE1310 (column: Ultra2) |
| Reactor | GC ISOLINK II |
| Interface | ConFlo IV |
| Mass spectrometer | DELTA V Advantage |
| Reactor temperature | 1000° C. |
| Column oven temperature | 40° C. (2.5 min)→temperature rise (20° C./min)→ 110° C. (0 min)→temperature rise (3.2° C./min)→ 150° C. (0 min)→temperature rise (9° C./min) 220° C. (17.3 min) |
| Carrier gas | He 1.4 ml/min |
| Standard gas | $N_2$ (purity: 99.999% or more) |
| Measurement of ion | 28, 29(m/z) |

(3) Measurement of Stable Carbon Isotope Ratio (δ13C)

The stable carbon isotope ratio (δ13C) of glutamic acid contained in a sample was measured by the following procedure.

Extraction Step (B1)

Distilled water and 1 M hydrogen chloride were added to a sample, followed by stirring for 10 minutes and then centrifugation. The precipitated insoluble components were removed.

Degreasing Step (B2)

TO the aqueous solution from which the insoluble components were removed was added a dichloromethane/n-hexane mixed solvent to perform liquid-liquid extraction. On this occasion, since an amino acid and fat or oil are selectively dissolved in the aqueous layer and the organic layer, respectively, the fat or oil was removed by collecting the aqueous layer only.

Column Purification Step (B3)

In the present invention, in order to simplify the purification step, the reverse phase chromatography step (B3-1) and the decolorization step (B3-2) were simultaneously performed. Specifically, porous spherical silica gel whose surface was modified with an octadecylsilyl group was placed in a polypropylene chromatographic column and was leveled until the silica gel interface became horizontal. Subsequently, column activated carbon was placed in the column to prepare a column for purification.

A sample was added to this column, and water was further added to the column as the mobile phase to remove lipids and pigments.

Cation Exchange Step (B4)

The amino acid was extracted under the following conditions:

Sample-cationizing agent: hydrogen chloride,
Stationary phase: "Amberlite IR120BH" manufactured by The Dow Chemical Company, and
Mobile phase: distilled water for removing impurities, and 10% ammonia solution for collecting the amino acid.

The resulting extract was vacuum-concentrated (60° C.) and was then dissolved in a distilled water/methanol mixture solution, followed by clarification by centrifugation and a hydrophilic PTFE filter ("Millex-LH" manufactured by MilliporeSigma).

Separation Step (B5)

Ammonium glutamate only was separated and purified by hydrophilic interaction liquid chromatography (HILIC). The conditions for HILIC were as follows:

Apparatus: "LC20AP" manufactured by Shimadzu Corporation,
Stationary phase: "Asahipak NH2P" manufactured by Showa Denko K.K., and
Mobile phase: aqueous ammonium hydrogen carbonate solution/methanol.

EA-IRMS Step (B6)

The δ13C was measured by EA-IRMS using 0.5 mg of ammonium glutamate placed on tin foil. The specification and the measurement conditions of the EA-IRMS system (manufactured by Thermo Fisher Scientific) were as shown in Table 2.

TABLE 2

| | |
|---|---|
| Elemental analyzer | FLASH2000 |
| Interface | ConFlo IV |
| Mass spectrometer | DELTA V Advantage |
| Combustion furnace temperature | 1000° C. |
| Reduction furnace temperature | 680° C. |
| Column temperature | 50° C. |
| Carrier gas | He 100 ml/min |
| Combustion gas | $O_2$ 175 ml/min |
| Reference gas | $CO_2$ (purity: 99.999% or more) |
| | $N_2$ (purity: 99.999% or more) |
| Measurement of ion | 44, 45, 46(m/z) |
| | 28, 29(m/z) |

Analysis Examples 1 to 34

The δ13C and δ15N of glutamic acid contained in samples 1 to 34 were measured according to the conditions shown in Tables 3 to 5.

First, samples 1 to 13 will be described. MSG 1 to 4 were monosodium glutamate (MSG) produced by fermenting carbohydrate contained in sugar cane and were acquired in Japan or Brazil. Similarly, MSG 5 to 10 were produced from maize, as a raw material, acquired in Brazil, China, Taiwan, or Thailand; and MSG 11 to 13 were produced from tapioca, as a raw material, acquired in India, Vietnam, or Thailand.

Samples 1 to 13 were monosodium glutamate (MSG) that had been separated and purified and were therefore not required to be purified again. Furthermore, unlike ammonium glutamate, there is no risk of decreasing the accuracy due to ammonia during the measurement. Accordingly, the δ13C and δ15N of samples 1 to 13 were measured by EA-IRMS only.

TABLE 3

| | | | Measurement example 1 | Measurement example 2 | Measurement example 3 | Measurement example 4 | Measurement example 5 | Measurement example 6 | Measurement example 7 |
|---|---|---|---|---|---|---|---|---|---|
| Sample | | | Sample 1 MSG1 | Sample 2 MSG2 | Sample 3 MSG3 | Sample 4 MSG4 | Sample 5 MSG5 | Sample 6 MSG6 | Sample 7 MSG7 |
| | | Acquisition place | Japan | Japan | Brazil | Brazil | Brazil | China | China |
| | | Raw material | Sugar cane | Sugar cane | Sugar cane | Sugar cane | Maize | Maize | Maize |
| | | Fermentation | Done | Done | Done | Done | Done | Done | Done |
| Hydrolysis | | | Unnecessary | Unnecessary | Unnecessary | Unnecessary | Unnecessary | Unnecessary | Unnecessary |
| δ15N | Extraction (A1) | | | | | Not performed | | | |
| | Degreasing (A2) | | | | | | | | |
| | Cation exchange (A3) | | | | | | | | |
| | Derivatization (A4) | Pivaloyl/ isopropyl ester | | | | | | | |
| δ13C | Extraction (B1) | | | | | | | | |
| | Degreasing (B2) | | | | | | | | |
| | Column purification (B3) | | | | | | | | |
| | Cation exchange (A3) | | | | | | | | |
| | Separation (B5) | HILIC | | | | | | | |
| Measurement result | δ15N | | −4.2 | −3.9 | −6.6 | −6.3 | −9.6 | −9.3 | −9.0 |
| | δ13C | | −15.6 | −16.0 | −13.3 | −13.3 | −10.9 | −10.1 | −10.7 |

| | | | Measurement example 8 | Measurement example 9 | Measurement example 10 | Measurement example 11 | Measurement example 12 | Measurement example 13 |
|---|---|---|---|---|---|---|---|---|
| Sample | | | Sample 8 MSG8 | Sample 9 MSG9 | Sample 10 MSG10 | Sample 11 MSG11 | Sample 12 MSG12 | Sample 13 MSG13 |
| | | Acquisition place | China | Taiwan | Thailand | India | Vietnam | Thailand |

TABLE 3-continued

|  |  | Raw material Fermentation | Maize Done Unnecessary | Maize Done Unnecessary | Maize Done Unnecessary | Tapioca Done Unnecessary | Tapioca Done Unnecessary | Tapioca Done Unnecessary |
|---|---|---|---|---|---|---|---|---|
| Hydrolysis |  |  |  |  | Not performed |  |  |  |
| δ15N | Extraction (A1) |  |  |  |  |  |  |  |
|  | Degreasing (A2) |  |  |  |  |  |  |  |
|  | Cation exchange (A3) |  |  |  |  |  |  |  |
|  | Derivatization (A4) | Pivaloyl/ isopropyl ester |  |  |  |  |  |  |
| δ13C | Extraction (B1) |  |  |  |  |  |  |  |
|  | Degreasing (B2) |  |  |  |  |  |  |  |
|  | Column purification (B3) |  |  |  |  |  |  |  |
|  | Cation exchange (A3) |  |  |  |  |  |  |  |
|  | Separation (B5) | HILIC |  |  |  |  |  |  |
| Measurement result | δ15N |  | −7.4 | −6.3 | −7.8 | −4.8 | −2.5 | −6.6 |
|  | δ13C |  | −12.3 | −15.0 | −11.6 | −29.1 | −26.2 | −26.1 |

Next, samples 14 to 22 will be described. Samples 14 to 22 were seasonings containing glutamates obtained by hydrolysis of protein contained in food. The raw material of seasonings 1 to 3 was maize, that of seasonings 4 to 6 was soybean, that of seasoning 7 was wheat, that of seasoning 8 was beet, and that of seasoning 9 was bonito. Since the samples had already been hydrolyzed, hydrolysis was not performed again.

TABLE 4

|  |  |  | Measurement example 14 | Measurement example 15 | Measurement example 16 | Measurement example 17 | Measurement example 18 |
|---|---|---|---|---|---|---|---|
| Sample |  |  | Sample 14 Seasoning 1 | Sample 15 Seasoning 2 | Sample 16 Seasoning 3 | Sample 17 Seasoning 4 | Sample 18 Seasoning 5 |
|  |  | Acquisition place | Japan | Japan | Japan | Japan | Japan |
|  |  | Raw material | Maize | Maize | Maize | Soybean | Soybean |
|  |  | Fermentation | Not done | Not done | Not done | Not done | Not done |
| Hydrolysis |  |  | Unnecessary (decomposed) | Unnecessary (decomposed) | Unnecessary (decomposed) | Unnecessary (decomposed) | Unnecessary (decomposed) |
| δ15N | Extraction (A1) |  | ○ | ○ | ○ | ○ | ○ |
|  | Degreasing (A2) |  |  |  |  |  |  |
|  | Cation exchange (A3) |  | ○ | ○ | ○ | ○ | ○ |
|  | Derivatization (A4) | Pivaloyl/ isopropyl ester | ○ | ○ | ○ | ○ | ○ |
| δ13C | Extraction (B1) |  | ○ | ○ | ○ | ○ | ○ |
|  | Degreasing (B2) |  |  |  |  |  |  |
|  | Column purification (B3) |  | ○ | ○ | ○ | ○ | ○ |
|  | Cation exchange (B4) |  | ○ | ○ | ○ | ○ | ○ |
|  | Separation (B5) |  | ○ | ○ | ○ | ○ | ○ |
| Measurement result | δ15N |  | 3.7 | −0.2 | −2.8 | 1.0 | −0.8 |
|  | δ13C |  | −13.5 | −12.6 | −12.7 | −21.5 | −24.1 |

|  |  |  | Measurement example 19 | Measurement example 20 | Measurement example 21 | Measurement example 22 |
|---|---|---|---|---|---|---|
| Sample |  |  | Sample 19 Seasoning 6 | Sample 20 Seasoning 7 | Sample 21 Seasoning 8 | Sample 22 Seasoning 9 |
|  |  | Acquisition place | Japan | Japan | Japan | Japan |
|  |  | Raw material | Soybean | Wheat | Beet | Bonito |
|  |  | Fermentation | Not done | Not done | Not done | Not done |
| Hydrolysis |  |  | Unnecessary (decomposed) | Unnecessary (decomposed) | Unnecessary (decomposed) | Unnecessary (decomposed) |
| δ15N | Extraction (A1) |  | ○ | ○ | ○ | ○ |
|  | Degreasing (A2) |  |  |  |  | ○ |
|  | Cation exchange (A3) |  | ○ | ○ | ○ | ○ |
|  | Derivatization (A4) | Pivaloyl/ isopropyl ester | ○ | ○ | ○ | ○ |
| δ13C | Extraction (B1) |  | ○ | ○ | ○ | ○ |
|  | Degreasing (B2) |  |  |  |  | ○ |
|  | Column purification (B3) |  | ○ | ○ | ○ | ○ |
|  | Cation exchange (B4) |  | ○ | ○ | ○ | ○ |
|  | Separation (B5) |  | ○ | ○ | ○ | ○ |
| Measurement result | δ15N |  | 2.0 | 2.4 | 0.5 | 23.5 |
|  | δ13C |  | −22.9 | −23.4 | −26.0 | −12.1 |

Lastly, samples 23 to 34 will be described. Samples 23 to 34 were tomato, Chinese cabbage, broccoli, dried shiitake mushroom, pork, kelp, cheese, chicken, sardine, and scallops. The degreasing step was performed or not performed depending on the amount of lipids.

According to the analysis results of measurement examples, glutamic acid was roughly classified into (1) glutamic acid prepared by fermenting carbohydrate derived from C3 plant (such as tapioca and wheat), (2) glutamic acid prepared by fermenting carbohydrate derived from C4 plant

TABLE 5

| | | | Measurement example 23 | Measurement example 24 | Measurement example 25 | Measurement example 26 | Measurement example 27 | Measurement example 28 |
|---|---|---|---|---|---|---|---|---|
| Sample | | | Sample 23 Perishable foodstuff 1 | Sample 24 Perishable foodstuff 2 | Sample 25 Perishable foodstuff 3 | Sample 26 Perishable foodstuff 4 | Sample 27 Perishable foodstuff 5 | Sample 28 Perishable foodstuff 6 |
| | | Acquisition place | Kumamoto Prefecture | Ibaraki Prefecture | Kumamoto Prefecture | Japan | Japan | Rausu-cho |
| | | Raw material | Tomato | Chinese cabbage | Broccoli | Dried shiitake mushroom | Pork | Kelp |
| | | Fermentation | Not done | Not done | Not done | Not done | Not done | Not done |
| Hydrolysis | | | Necessary | Necessary | Necessary | Necessary | Necessary | Necessary |
| $\delta^{15}N$ | Extraction (A1) | | ○ | ○ | ○ | ○ | ○ | ○ |
| | Degreasing (A2) | | | | | | ○ | |
| | Cation exchange (A3) | | ○ | ○ | ○ | ○ | ○ | ○ |
| | Derivatization (A4) | Pivaloyl/ isopropyl ester | ○ | ○ | ○ | ○ | ○ | ○ |
| $\delta^{13}C$ | Extraction (B1) | | ○ | ○ | ○ | ○ | ○ | ○ |
| | Degreasing (B2) | | | | | | ○ | |
| | Column purification (B3) | | ○ | ○ | ○ | ○ | ○ | ○ |
| | Cation exchange (B4) | | ○ | ○ | ○ | ○ | ○ | ○ |
| | Separation (B5) | | ○ | ○ | ○ | ○ | ○ | ○ |
| Measurement result | $\delta^{15}N$ | | 6.4 | −2.4 | 2.1 | 2.8 | 1.6 | 7.2 |
| | $\delta^{13}C$ | | −27.3 | −23.6 | −26.6 | −22.6 | −13.0 | −10.0 |
| | | | Measurement example 29 | Measurement example 30 | Measurement example 31 | Measurement example 32 | Measurement example 33 | Measurement example 34 |
| Sample | | | Sample 29 Perishable foodstuff 7 | Sample 30 Perishable foodstuff 8 | Sample 31 Perishable foodstuff 9 | Sample 32 Perishable foodstuff 10 | Sample 33 Perishable foodstuff 11 | Sample 34 Perishable foodstuff 12 |
| | | Acquisition place | Rishiri-cho | Hidaka-shi | Japan | Japan | Mie Prefecture | Hokkaido |
| | | Raw material | Kelp | Kelp | Cheese | Chicken | Sardine | Scallops |
| | | Fermentation | Not done | Not done | Not done | Not done | Not done | Not done |
| Hydrolysis | | | Necessary | Necessary | Necessary | Necessary | Necessary | Necessary |
| $\delta^{15}N$ | Extraction (A1) | | ○ | ○ | ○ | ○ | ○ | ○ |
| | Degreasing (A2) | | | | ○ | ○ | ○ | ○ |
| | Cation exchange (A3) | | ○ | ○ | ○ | ○ | ○ | ○ |
| | Derivatization (A4) | Pivaloyl/ isopropyl ester | ○ | ○ | ○ | ○ | ○ | ○ |
| $\delta^{13}C$ | Extraction (B1) | | ○ | ○ | ○ | ○ | ○ | ○ |
| | Degreasing (B2) | | | | | | | |
| | Column purification (B3) | | ○ | ○ | ○ | ○ | ○ | ○ |
| | Cation exchange (B4) | | ○ | ○ | ○ | ○ | ○ | ○ |
| | Separation (B5) | | ○ | ○ | ○ | ○ | ○ | ○ |
| Measurement result | $\delta^{15}N$ | | 4.0 | 8.3 | 5.2 | 1.3 | 12.6 | 11.2 |
| | $\delta^{13}C$ | | −10.4 | −12.0 | −18.1 | −13.1 | −14.6 | −16.7 |

FIG. 1 shows the measurement results of analysis examples 1 to 34 (vertical axis: $\delta^{13}C$(‰), horizontal axis: $\delta^{15}N$(‰)).

In FIG. 1, "o" indicates monosodium glutamate (MSG) produced by fermenting carbohydrate contained in sugar cane, "Δ" indicates MSG produced by fermenting carbohydrate contained in maize, "□" indicates MSG produced by fermenting carbohydrate contained in tapioca, "▲" indicates a glutamate prepared by hydrolyzing protein contained in maize, "■" indicates a glutamate prepared by hydrolyzing protein contained in soybean, wheat, or the like, "♦" indicates a glutamate prepared by hydrolyzing protein contained in kelp, "•" indicates a glutamate prepared by hydrolyzing protein contained in fish or shellfish, "x" indicates a glutamate prepared by hydrolyzing protein contained in meat, and "*" indicates a glutamate prepared by hydrolyzing protein contained in other food.

(such as sugar cane and maize), (3) glutamic acid prepared by hydrolyzing protein contained in C3 plant, (4) glutamic acid prepared by hydrolyzing protein contained in C4 plant or meat obtained by feeding with C4 plant, (5) glutamic acid prepared by hydrolyzing protein contained in kelp, and (6) glutamic acid prepared by hydrolyzing protein contained in fish or shellfish.

Examples 1 to 13

The $\delta^{13}C$ and $\delta^{15}N$ of glutamic acid in samples 101 to 113 in which the origins of the raw materials were unclear were measured. Unlike the cases of analysis examples 1 to 34, since the impurities (such as lipids and amino acids other than glutamic acid) contained in samples 101 to 113 were not clear, all purification steps were performed.

Figure 2:
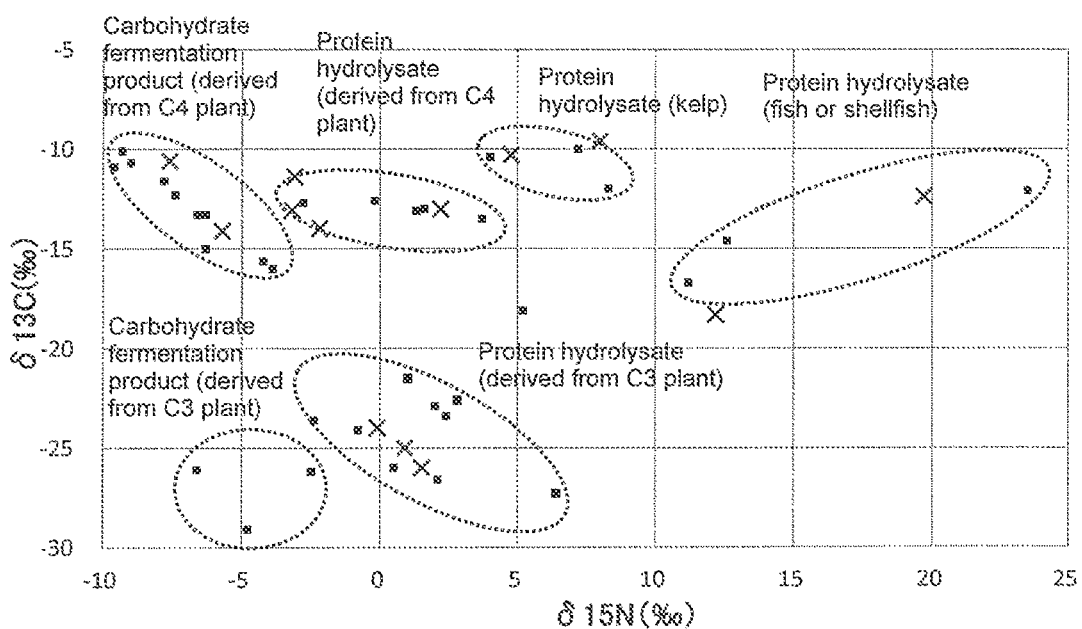
FIG. 2 is a graph plotting, in the graph of FIG. 1, the stable isotope ratios of glutamic acid contained in samples whose origins are unclear.

In FIG. 2, the stable isotope ratios of samples whose origins were unclear were indicated by "x", and the stable isotope ratios of samples whose origins were clear were indicated by "■".

The origins of Examples 1 to 13 predicted by comparison with analysis examples 1 to 34 were as follows.

TABLE 6

|   |   | Example 1 | Example 2 | Example 3 | Example 4 | Example 5 | Example 6 | Example 7 |
|---|---|---|---|---|---|---|---|---|
| δ15N |   | Sample 101<br>−5.7 | Sample 102<br>−7.6 | Sample 103<br>−3.1 | Sample 104<br>12.2 | Sample 105<br>0.9 | Sample 106<br>−3.2 | Sample 107<br>−2.2 |
| δ13C |   | −14.1 | −10.6 | −11.4 | −18.3 | −25.0 | −13.1 | −14.0 |
| Predicted origin | Raw material | C4 plant | C4 plant | C4 plant | Small fish or shellfish such as scallops | C3 plant | C4 plant | C4 plant |
|   | Preparation | Fermentation (MSG) | Fermentation (MSG) | Hydrolysis | Hydrolysis | Hydrolysis | Hydrolysis | Hydrolysis |

|   |   | Example 8 | Example 9 | Example 10 | Example 11 | Example 12 | Example 13 |
|---|---|---|---|---|---|---|---|
| δ15N |   | Sample 108<br>19.7 | Sample 109<br>−0.1 | Sample 110<br>1.5 | Sample 111<br>2.2 | Sample 112<br>4.8 | Sample 113<br>8.0 |
| δ13C |   | −12.4 | −24.0 | −26.0 | −13.0 | −10.3 | −9.6 |
| Predicted origin | Raw material | Large fish or shellfish such as bonito | C3 plant | C3 plant | C4 plant or meat | Kelp | Kelp |
|   | Preparation | Hydrolysis | Hydrolysis | Hydrolysis | Hydrolysis | Hydrolysis | Hydrolysis |

In general, since large fish or shellfish, which are higher in the food chain, tend to have higher δ15N, it was predicted that the sample of Example 4 was glutamic acid derived from small fish or shellfish, such as shellfish and sardine, and that the sample of Example 8 was glutamic acid derived from large fish or shellfish, such as bonito and tuna.

In Example 11, since the δ15N was −3.5 to 5‰ and the δ13C was −15‰ or more, it was predicted that the sample was not MSG but glutamic acid derived from C4 plant (such as maize and sugar cane) or meat. In livestock industry, since maize is often used as feed, meat is apt to have an isotope ratio close to those of C4 plant, and it is probably difficult to discriminate the both.

(Verification of Accuracy)

The isotope fractionation of δ13C in the purification steps (B1) to (B5) was verified as follows.

Table 7 shows the results of measurement of δ13C of a reagent, L(+)-monosodium glutamate hydrate (manufactured by FUJIFILM Wako Pure Chemical Corporation, 98%-102%), by EA-IRMS when no purification was performed, when only the extraction step (B1) was performed, when only the degreasing step (B2) was performed, when only the column purification step (B3) was performed, when only the cation exchange step (B4) was performed, when only the separation step (B5) was performed, and when all the purification steps were performed.

TABLE 7

| Step | δ13C (‰) |
|---|---|
| Reagent only (no purification) | −14.0 |
| Extraction (B1) | −14.2 |
| Degreasing (B2) | −14.2 |
| Column purification (B3) | −14.2 |
| Cation exchange (B4) | −14.8 |
| Separation (B5) | −14.1 |
| All purification steps | −14.1 |

According to Table 7, carbon isotope fractionation hardly occurs when the extraction step (B1), the degreasing step (B2), the column purification step (B3), the separation step (B5), and all the purification steps were performed. Accordingly, "liquid-liquid extraction", "removal of fat or oil component by reverse phase chromatography", "removal of pigment component with activated carbon column", and "separation and purification of amino acid by hydrophilic interaction liquid chromatography" are purification methods that hardly cause isotope fractionation and can be used in arbitrary combination thereof for purification of an amino acid.

In contrast, carbon isotope fractionation readily occurs in the cation exchange step. Accordingly, the cation exchange step is preferably performed in combination with another purification step, without being performed alone.

Since nitrogen isotope fractionation hardly occurs in the cation exchange step (Non Patent Literature 3), in the measurement of δ15N, it is not necessary to note isotope fractionation by cation exchange.

The invention claimed is:

1. A method for measuring a stable isotope ratio of glutamic acid, the method comprising:
   (a) measuring a stable carbon isotope ratio (δ13C) of the glutamic acid, comprising:
      separating and purifying glutamic acid in a first sample containing the glutamic acid by hydrophilic interaction liquid chromatography, as a first pretreatment, so as to obtain a first pretreated sample; and
      measuring the δ13C of the glutamic acid contained in the first pretreated sample by elemental analysis-stable isotope ratio mass spectrometry (EA-IRMS), wherein the δ13C is not measured by gas chromatography-stable isotope ratio mass spectrometry (GC-IRMS); and
   (b) measuring a stable nitrogen isotope ratio (δ15N) of the glutamic acid, comprising:
      pretreating a second sample containing the glutamic acid so as to obtain a second pretreated sample, as a second pretreatment, the second pretreatment comprising:
         cation-exchanging the second sample, with a cation-exchange column, and then derivatizing the glutamic acid in the second sample, so that the second pretreated sample is obtained; and measuring the δ15N of the glutamic acid contained in the second pretreated sample, by GC-IRMS, wherein the δ15N is not measured by EA-IRMS.

2. The method for measuring a stable isotope ratio of glutamic acid according to claim 1, the first pretreatment further comprising:

removing a fat or oil component by reverse phase chromatography for measuring the δ13C, before the hydrophilic interaction liquid chromatography.

3. The method for measuring a stable isotope ratio of glutamic acid according to claim 1, the first pretreatment further comprising:

removing a pigment component using an activated carbon column for measuring the δ13C, before the hydrophilic interaction liquid chromatography.

4. A method for determining an origin of glutamic acid whose origin is unclear, the method comprising:

comparing a stable carbon isotope ratio (δ13C) and a stable nitrogen isotope ratio (δ15N) of glutamic acid contained in a sample whose origin is clear and a stable carbon isotope ratio (δ13C) and a stable nitrogen isotope ratio (δ15N) of glutamic acid contained in a sample whose origin is unclear; and determining the origin of the glutamic acid, wherein the δ13C and the δ15N of the glutamic acid contained in the sample whose origin is unclear are measured by the method according to claim 1.

5. The method for measuring a stable isotope ratio of glutamic acid according to claim 1, wherein the first pretreatment for the measuring the δ13C further comprises, before the separating and purifying by the hydrophilic interaction liquid chromatography:

(a') at least one procedure selected from the group consisting of:

extracting from a sample for measuring the δ13C, soluble components by precipitating insoluble components in the first sample for measuring the δ13C with a solution comprising hydrogen chloride, and removing the insoluble components, column-purifying the soluble components, the column-purifying comprising: removing a fat or oil component by reverse phase chromatography, and removing a pigment component using an activated carbon column, and cation-exchanging the first sample for measuring the δ13C with a cation-exchange column, wherein the extracting, the column-purifying, and the cation-exchanging are performed in this order if two or three thereof are present in the first pretreatment, and wherein the second pretreatment for the measuring the δ15N further comprises, before the cation-exchanging, (b') for the measuring the δ15N, at least one procedure selected from the group consisting of:

extracting from the second sample for measuring the δ15N, soluble components by precipitating insoluble components in the second sample with a solution comprising hydrogen chloride, and removing the insoluble components.

6. A method for measuring a stable isotope ratio of an amino acid, the method comprising:

(a) measuring a stable carbon isotope ratio (δ13C ) of the amino acid, comprising:

separating and purifying the amino acid in a first sample containing the amino acid by hydrophilic interaction liquid chromatography, as a first pretreatment, so as to obtain a first pretreated sample; and measuring the δ13C of the amino acid contained in the first pretreated sample by elemental analysis-stable isotope ratio mass spectrometry (EA-IRMS), wherein the δ13C is not measured by gas chromatography-stable isotope ratio mass spectrometry (GC-IRMS); and (b) measuring a stable nitrogen isotope ratio (δ15N) of the glutamic acid, comprising:

pretreating a second sample containing the amino acid so as to obtain a second pretreated sample, as a second pretreatment, the second pretreatment comprising:

cation-exchanging the second sample, with a cation-exchange column, and then derivatizing the amino acid in the second sample, so that the second pretreated sample is obtained; and measuring the δ15N a stable nitrogen isotope ratio (δ15N) of the amino acid contained in the second pretreated sample by GC-IRMS, wherein the δ15N is not measured by EA-IRMS.

7. The method for measuring a stable isotope ratio of an amino acid according to claim 6, the first pretreatment further comprising:

removing a fat or oil component by reverse phase chromatography for measuring the δ13C, before the hydrophilic interaction liquid chromatography.

8. The method for measuring a stable isotope ratio of an amino acid according to claim 6, the first pretreatment further comprising:

removing a pigment component using an activated carbon column for measuring the δ13C, before the hydrophilic interaction liquid chromatography.

9. A method for determining an origin of an amino acid whose origin is unclear, comprising:

comparing a stable carbon isotope ratio (δ13C) and a stable nitrogen isotope ratio (δ15N) of an amino acid contained in a sample whose origin is clear and a stable carbon isotope ratio (δ13C) and a stable nitrogen isotope ratio (δ15N) of an amino acid contained in a sample whose origin is unclear; and determining the origin of the amino acid, wherein the stable carbon isotope ratio (δ13C) and the stable nitrogen isotope ratio (δ15N) of the amino acid contained in the sample whose origin is unclear are measured by the method according to claim 6.

10. The method for measuring a stable isotope ratio of amino acid according to claim 6, wherein the first pretreatment for the measuring the δ13C further comprises, before the separating and purifying by the hydrophilic interaction liquid chromatography:

(a') at least one procedure selected from the group consisting of:

extracting from the first sample for measuring the δ13C, soluble components by precipitating insoluble components in the first sample for measuring the δ13C with a solution comprising hydrogen chloride, and removing the insoluble components, column-purifying the soluble components, the column-purifying comprising: removing a fat or oil component by reverse phase chromatography, and removing a pigment component using an activated carbon column, and cation-exchanging the first sample for measuring the δ13C with a cation-exchange column,
wherein the extracting, the column-purifying, and the cation-exchanging are performed in this order if two or three thereof are present in the first pretreatment, and wherein the second pretreatment for the measuring the δ15N further comprises, before the cation-exchanging, (b')
extracting from the second sample for measuring the δ15N, soluble components by precipitating insoluble components in the second sample for measuring the δ15N with a solution comprising hydrogen chloride, and removing the insoluble components.

* * * * *